United States Patent [19]

Kanmera et al.

[11] Patent Number: 5,229,489
[45] Date of Patent: Jul. 20, 1993

[54] PARATHYROID HORMONE ANTAGONISTS

[75] Inventors: Tatsuhiko Kanmera, Yokohama; Akihisa Mori; Yoshihide Nakao, both of Machida; Toshihiko Minegishi, Yokohama, all of Japan

[73] Assignee: Mitsubishi Kasei Corporation, Tokyo, Japan

[21] Appl. No.: 684,391

[22] Filed: Apr. 12, 1991

[30] Foreign Application Priority Data

Apr. 12, 1990 [JP] Japan .................................. 2-96952

[51] Int. Cl.$^5$ .............................................. C07K 7/10
[52] U.S. Cl. .................................... 530/324; 530/325; 514/12; 514/2; 930/DIG. 821; 930/DIG. 820; 930/DIG. 800
[58] Field of Search ................ 530/324, 325; 514/12, 514/2; 930/DIG. 821, DIG. 820, DIG. 800

[56] References Cited

U.S. PATENT DOCUMENTS

| | | | |
|---|---|---|---|
| 3,886,132 | 5/1975 | Brewer et al. | 530/324 |
| 4,423,037 | 12/1983 | Rosenblatt et al. | 530/324 |
| 4,656,250 | 4/1987 | Morita et al. | 530/324 |

FOREIGN PATENT DOCUMENTS

| | | |
|---|---|---|
| 0293158A2 | 11/1988 | European Pat. Off. . |
| 0293160A2 | 11/1988 | European Pat. Off. . |
| 0341962A2 | 11/1989 | European Pat. Off. . |
| 0341963A2 | 11/1989 | European Pat. Off. . |

OTHER PUBLICATIONS

Rosenblatt et al, Biochemistry, vol. 20, pp. 7246–7250, (1981).
McKee et al, Endocrinology, vol. 127, No. 1, pp. 76–82, (1990).
Nutt et al, Endocrinology, vol. 127, No. 1, pp. 491–493, (1990).
Horiuchi et al, Science, vol. 238, pp. 1566–1568, (1987).
Juppner et al, Biochemistry, vol. 29, No. 30, pp. 6941–6946, (1990).
Strewler et al, The Journal of Clinical Investigation, vol. 80, pp. 1803–1807, (1987).
Donahue et al, Endocrinology, vol. 126, No. 3, pp. 1471–1477, (1990).
Goltzmann et al, The Journal of Biological Chemistry, vol. 250, No. 8, pp. 3199–3203, (1975).
Cohen et al, The Journal of Biological Chemistry, vol. 266, No. 3, pp. 1997–2004, (1991).
Mosley et al, Proc. Natl. Acad. Sci. USA, vol. 84, pp. 5048–5052 (1987).
Suva et al, Science, vol. 237, pp. 893–896, (1987).
Coltrera et al, American Chemical Society, vol. 19, No. 18, pp. 4380–4384, (1980).
Mangin et al, Proc. Nat'l. Acad. Sci. USA, vol. 85, pp. 597–601, (1988).
Chemical Abstracts, vol. 105, No. 25, Dec. 25, 1986, col. 218917n.

*Primary Examiner*—Merrell C. Cashion, Jr.
*Assistant Examiner*—T. D. Wessendorf
*Attorney, Agent, or Firm*—Wenderoth, Lind & Ponack

[57] ABSTRACT

Peptide derivatives of the following general formula (I): Seq. ID Nos. 1-6.

```
AAA BBB CCC DDD EEE FFF His GGG HHH Gly Lys Ser      (I)
 1           5                      10

Ile Gln Asp Leu Arg Arg Arg Phe Phe Leu III JJJ Leu Ile Ala
         15              20                25

Glu Ile His Thr Xaa
                                                  30
``` wherein AAA is deletion or Ser, BBB is deletion or Glu, CCC is deletion, Ile, Phe, Leu, cyclohexylalanine, D-alle or Lys substituted at the ε-position by $C_6$–$C_{18}$ alkylcarbonyl group, DDD is Gly or Gln, EEE is Leu, Nle or Phe, FFF is Met, Leu or Nle, GGG is Ala, Ser, Leu, Asn, Asp or Gln, HHH is Leu, Glu or Lys, III is His, Lys or Arg, JJJ is His, Lys or Arg, Xaa is Ala modified at the carboxy terminal with an amino group, provided that CCC and DDD may independently be modified at the amino terminal by $C_2$–$C_{18}$ alkylcarbonyl group, and that EEE is not Leu when FFF is Met, GGG is Asn, HHH is Leu, III and JJJ are His, and the salts thereof, which exhibit a potent inhibitory activity against hPTH and are useful as a therapeutic agent for treating dysbolism associated with calcium or phosphoric acid, such as hypercalcemia, osteoporosis, hyperparathyroidism, renal osteodystrophy, and the like, and other related diseases involving PTH or PTHrP.

1 Claim, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 32 amino acids
        ( B ) TYPE: Amino acid
        ( C ) STRANDEDNESS: single
        ( D ) TOPOLOGY: unknown ( i x ) FEATURE:
        ( A ) NAME/KEY: modified-site
        ( B ) LOCATION: 3
        ( C ) IDENTIFICATION METHOD:
        ( D ) OTHER INFORMATION: /note="Ile, Phe, Leu, cyclohexylalanine, D-alle or Lys substituted at the epsilon-position by C6-C18 alkylcarbonyl group, which may be modified at the amino terminal by C2-C18 alkylcarbonyl grp."

( i x ) FEATURE:
        ( A ) NAME/KEY: modified-site
        ( B ) LOCATION: 4
        ( C ) IDENTIFICATION METHOD:
        ( D ) OTHER INFORMATION: /note="Gly or Gln, which may be modified at the amino terminal by C2-C18 alkylcarbonyl group"

( i x ) FEATURE:
        ( A ) NAME/KEY: modified-site
        ( B ) LOCATION: 5
        ( C ) IDENTIFICATION METHOD:
        ( D ) OTHER INFORMATION: /note="Leu, Nle or Phe, provided that this amino acid is not Leu when the amino acid at location 6 is Met, the amino acid at location 8 is Asn, the amino acid at location 9 is Leu, and the amino acids at locations 23 and 24 are both His"

( i x ) FEATURE:
        ( A ) NAME/KEY: modified-site
        ( B ) LOCATION: 6
        ( C ) IDENTIFICATION METHOD:
        ( D ) OTHER INFORMATION: /note="Met, Leu or Nle"

( i x ) FEATURE:

(A) NAME/KEY: modified-site
                    (B) LOCATION: 8
                    (C) IDENTIFICATION METHOD:
                    (D) OTHER INFORMATION: /note="Ala, Ser, Leu,
Asn, Asp or Gln"

(ix) FEATURE:
                    (A) NAME/KEY: modified-site
                    (B) LOCATION: 9
                    (C) IDENTIFICATION METHOD:
                    (D) OTHER INFORMATION: /note="Leu, Glu or Lys"

(ix) FEATURE:
                    (A) NAME/KEY: modified-site
                    (B) LOCATION: 23
                    (C) IDENTIFICATION METHOD:
                    (D) OTHER INFORMATION: /note="His, Lys or Arg"

(ix) FEATURE:
                    (A) NAME/KEY: modified-site
                    (B) LOCATION: 24
                    (C) IDENTIFICATION METHOD:
                    (D) OTHER INFORMATION: /note="His, Lys, or Arg"

(ix) FEATURE:
                    (A) NAME/KEY: modified-site
                    (B) LOCATION: 32
                    (C) IDENTIFICATION METHOD:
                    (D) OTHER INFORMATION: /note="Ala modified at
the carboxy terminal with an amino group"

(xi) SEQUENCE DESCRIPTION: SEQ ID NO:1:

Ser Glu Xaa Xaa Xaa Xaa His Xaa Xaa Gly Lys Ser Ile Gln Asp
 1               5                   10                  15

Leu Arg Arg Arg Phe Phe Leu Xaa Xaa Leu Ile Ala Glu Ile His
                20                  25                  30

Thr Xaa (2) INFORMATION FOR SEQ ID NO:2:

(i) SEQUENCE CHARACTERISTICS:
                    (A) LENGTH: 31 amino acids
                    (B) TYPE: Amino acid
                    (C) STRANDEDNESS: single
                    (D) TOPOLOGY: unknown (ix) FEATURE:
                    (A) NAME/KEY: modified-site
                    (B) LOCATION: 2
                    (C) IDENTIFICATION METHOD:
                    (D) OTHER INFORMATION: /note="Ile, Phe, Leu,
cyclohexylalanine, D-alle or Lys substituted at the
epsilon-position by C6-C18 alkylcarbonyl group, which may be
modified at the amino terminal by C2-C18 alkylcarbonyl
group"

(ix) FEATURE:
                    (A) NAME/KEY: modified-site
                    (B) LOCATION: 3
                    (C) IDENTIFICATION METHOD:
                    (D) OTHER INFORMATION: /note="Gly or Gln, which
may be modified at the amino terminal by C2-C18
alkylcarbonyl group"

(ix) FEATURE:
                    (A) NAME/KEY: modified-site
                    (B) LOCATION: 4
                    (C) IDENTIFICATION METHOD:
                    (D) OTHER INFORMATION: /note="Leu, Nle or Phe,
provided that this amino acid is not Leu when the amino acid
at location 5 is Met, the amino acid at location 7 is Asn,
the amino acid at location 8 is Leu, and the amino acids at
locations 22 and 23 are both His"

(ix) FEATURE:
                    (A) NAME/KEY: modified-site
                    (B) LOCATION: 5
                    (C) IDENTIFICATION METHOD:

(D) OTHER INFORMATION: /note="Met, Leu or Nle"

(ix) FEATURE:
    (A) NAME/KEY: modified-site
    (B) LOCATION: 7
    (C) IDENTIFICATION METHOD:
    (D) OTHER INFORMATION: /note="Ala, Ser, Leu, Asn, Asp or Gln"

(ix) FEATURE:
    (A) NAME/KEY: modified-site
    (B) LOCATION: 8
    (C) IDENTIFICATION METHOD:
    (D) OTHER INFORMATION: /note="Leu, Glu or Lys"

(ix) FEATURE:
    (A) NAME/KEY: modified-site
    (B) LOCATION: 22
    (C) IDENTIFICATION METHOD:
    (D) OTHER INFORMATION: /note="His, Lys or Arg"

(ix) FEATURE:
    (A) NAME/KEY: modified-site
    (B) LOCATION: 23
    (C) IDENTIFICATION METHOD:
    (D) OTHER INFORMATION: /note="His, Lys, or Arg"

(ix) FEATURE:
    (A) NAME/KEY: modified-site
    (B) LOCATION: 31
    (C) IDENTIFICATION METHOD:
    (D) OTHER INFORMATION: /note="Ala modified at the carboxy terminal with an amino group"

(xi) SEQUENCE DESCRIPTION: SEQ ID NO:2:

| Glu | Xaa | Xaa | Xaa | Xaa | His | Xaa | Xaa | Gly | Lys | Ser | Ile | Gln | Asp | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Arg | Arg | Arg | Phe | Phe | Leu | Xaa | Xaa | Leu | Ile | Ala | Glu | Ile | His | Thr |
|     |     |     |     | 20  |     |     |     |     | 25  |     |     |     |     | 30  |
| Xaa |     |     |     |     |     |     |     |     |     |     |     |     |     |     |

(2) INFORMATION FOR SEQ ID NO:3:

(i) SEQUENCE CHARACTERISTICS:
        (A) LENGTH: 30 amino acids
        (B) TYPE: Amino acid
        (C) STRANDEDNESS: single
        (D) TOPOLOGY: unknown (ix) FEATURE:
    (A) NAME/KEY: modified-site
    (B) LOCATION: 1
    (C) IDENTIFICATION METHOD:
    (D) OTHER INFORMATION: /note="Ile, Phe, Leu, cyclohexylalanine, D-alle or Lys substituted at the epsilon-position by C6-C18 alkylcarbonyl group, which may be modified at the amino terminal by C2-C18 alkylcarbonyl group"

(ix) FEATURE:
    (A) NAME/KEY: modified-site
    (B) LOCATION: 2
    (C) IDENTIFICATION METHOD:
    (D) OTHER INFORMATION: /note="Gly or Gln, which may be modified at the amino terminal by C2-C18 alkylcarbonyl group"

(ix) FEATURE:
    (A) NAME/KEY: modified-site
    (B) LOCATION: 3
    (C) IDENTIFICATION METHOD:
    (D) OTHER INFORMATION: /note="Leu, Nle or Phe, provided that this amino acid is not Leu when the amino acid at location 4 is Met, the amino acid at location 6 is Asn, the amino acid at location 7 is Leu, and the amino acids at locations 21 and 22 are both His"

(ix) FEATURE:

(A) NAME/KEY: modified-site
                (B) LOCATION: 4
                (C) IDENTIFICATION METHOD:
                (D) OTHER INFORMATION: /note="Met, Leu or Nle"

(ix) FEATURE:
                (A) NAME/KEY: modified-site
                (B) LOCATION: 6
                (C) IDENTIFICATION METHOD:
                (D) OTHER INFORMATION: /note="Ala, Ser, Leu,
Asn, Asp or Gln"

(ix) FEATURE:
                (A) NAME/KEY: modified-site
                (B) LOCATION: 7
                (C) IDENTIFICATION METHOD:
                (D) OTHER INFORMATION: /note="Leu, Glu or Lys"

(ix) FEATURE:
                (A) NAME/KEY: modified-site
                (B) LOCATION: 21
                (C) IDENTIFICATION METHOD:
                (D) OTHER INFORMATION: /note="His, Lys or Arg"

(ix) FEATURE:
                (A) NAME/KEY: modified-site
                (B) LOCATION: 22
                (C) IDENTIFICATION METHOD:
                (D) OTHER INFORMATION: /note="His, Lys, or Arg"

(ix) FEATURE:
                (A) NAME/KEY: modified-site
                (B) LOCATION: 30
                (C) IDENTIFICATION METHOD:
                (D) OTHER INFORMATION: /note="Ala modified at
the carboxy terminal with an amino group"

(xi) SEQUENCE DESCRIPTION: SEQ ID NO:3:

Xaa  Xaa  Xaa  Xaa  His  Xaa  Xaa  Gly  Lys  Ser  Ile  Gln  Asp  Leu  Arg
 1                    5                         10                        15

Arg  Arg  Phe  Phe  Leu  Xaa  Xaa  Leu  Ile  Ala  Glu  Ile  His  Thr  Xaa
                     20                        25                        30

(2) INFORMATION FOR SEQ ID NO:4:

(i) SEQUENCE CHARACTERISTICS:
                (A) LENGTH: 29 amino acids
                (B) TYPE: Amino acid
                (C) STRANDEDNESS: single
                (D) TOPOLOGY: unknown (ix) FEATURE:
                (A) NAME/KEY: modified-site
                (B) LOCATION: 1
                (C) IDENTIFICATION METHOD:
                (D) OTHER INFORMATION: /note="Gly or Gln, which
may be modified at the amino terminal by C2-C18
alkylcarbonyl group"

(ix) FEATURE:
                (A) NAME/KEY: modified-site
                (B) LOCATION: 2
                (C) IDENTIFICATION METHOD:
                (D) OTHER INFORMATION: /note="Leu, Nle or Phe,
provided that this amino acid is not Leu when the amino acid
at location 3 is Met, the amino acid at location 5 is Asn,
the amino acid at location 6 is Leu, and the amino acids at
locations 20 and 21 are both His"

(ix) FEATURE:
                (A) NAME/KEY: modified-site
                (B) LOCATION: 3
                (C) IDENTIFICATION METHOD:
                (D) OTHER INFORMATION: /note="Met, Leu or Nle"

(ix) FEATURE:
                (A) NAME/KEY: modified-site
                (B) LOCATION: 5
                (C) IDENTIFICATION METHOD:

(D) OTHER INFORMATION: /note="Ala, Ser, Leu, Asn, Asp or Gln"

(ix) FEATURE:
  (A) NAME/KEY: modified-site
  (B) LOCATION: 6
  (C) IDENTIFICATION METHOD:
  (D) OTHER INFORMATION: /note="Leu, Glu or Lys"

(ix) FEATURE:
  (A) NAME/KEY: modified-site
  (B) LOCATION: 20
  (C) IDENTIFICATION METHOD:
  (D) OTHER INFORMATION: /note="His, Lys or Arg"

(ix) FEATURE:
  (A) NAME/KEY: modified-site
  (B) LOCATION: 21
  (C) IDENTIFICATION METHOD:
  (D) OTHER INFORMATION: /note="His, Lys, or Arg"

(ix) FEATURE:
  (A) NAME/KEY: modified-site
  (B) LOCATION: 29
  (C) IDENTIFICATION METHOD:
  (D) OTHER INFORMATION: /note="Ala modified at the carboxy terminal with an amino group"

(xi) SEQUENCE DESCRIPTION: SEQ ID NO:4:

Xaa Xaa Xaa His Xaa Xaa Gly Lys Ser Ile Gln Asp Leu Arg Arg
 1               5                   10                  15

Arg Phe Phe Leu Xaa Xaa Leu Ile Ala Glu Ile His Thr Xaa
              20                  25

(2) INFORMATION FOR SEQ ID NO:5:

(i) SEQUENCE CHARACTERISTICS:
    (A) LENGTH: 30 amino acids
    (B) TYPE: Amino acid
    (C) STRANDEDNESS: single
    (D) TOPOLOGY: unknown (ix) FEATURE:
    (A) NAME/KEY: modified-site
    (B) LOCATION: 2
    (C) IDENTIFICATION METHOD:
    (D) OTHER INFORMATION: /note="Gly or Gln, which may be modified at the amino terminal by C2-C18 alkylcarbonyl group"

(ix) FEATURE:
    (A) NAME/KEY: modified-site
    (B) LOCATION: 3
    (C) IDENTIFICATION METHOD:
    (D) OTHER INFORMATION: /note="Leu, Nle or Phe, provided that this amino acid is not Leu when the amino acid at location 4 is Met, the amino acid at location 6 is Asn, the amino acid at location 7 is Leu, and the amino acids at locations 21 and 22 are both His"

(ix) FEATURE:
    (A) NAME/KEY: modified-site
    (B) LOCATION: 4
    (C) IDENTIFICATION METHOD:
    (D) OTHER INFORMATION: /note="Met, Leu or Nle"

(ix) FEATURE:
    (A) NAME/KEY: modified-site
    (B) LOCATION: 6
    (C) IDENTIFICATION METHOD:
    (D) OTHER INFORMATION: /note="Ala, Ser, Leu, Asn, Asp or Gln"

(ix) FEATURE:
    (A) NAME/KEY: modified-site
    (B) LOCATION: 7
    (C) IDENTIFICATION METHOD:
    (D) OTHER INFORMATION: /note="Leu, Glu or Lys"

( i x ) FEATURE:
    ( A ) NAME/KEY: modified-site
    ( B ) LOCATION: 21
    ( C ) IDENTIFICATION METHOD:
    ( D ) OTHER INFORMATION: /note="His, Lys or Arg"

( i x ) FEATURE:
    ( A ) NAME/KEY: modified-site
    ( B ) LOCATION: 22
    ( C ) IDENTIFICATION METHOD:
    ( D ) OTHER INFORMATION: /note="His, Lys, or Arg"

( i x ) FEATURE:
    ( A ) NAME/KEY: modified-site
    ( B ) LOCATION: 30
    ( C ) IDENTIFICATION METHOD:
    ( D ) OTHER INFORMATION: /note="Ala modified at the carboxy terminal with an amino group"

( x i ) SEQUENCE DESCRIPTION: SEQ ID NO:5:

```
Ser Xaa Xaa Xaa His Xaa Xaa Gly Lys Ser Ile Gln Asp Leu Arg
 1               5                  10                  15

Arg Arg Phe Phe Leu Xaa Xaa Leu Ile Ala Glu Ile His Thr Xaa
                20                  25                  30
```

( 2 ) INFORMATION FOR SEQ ID NO:6:

( i ) SEQUENCE CHARACTERISTICS:
        ( A ) LENGTH: 31 amino acids
        ( B ) TYPE: Amino acid
        ( C ) STRANDEDNESS: single
        ( D ) TOPOLOGY: unknown ( i x ) FEATURE:
    ( A ) NAME/KEY: modified-site
    ( B ) LOCATION: 3
    ( C ) IDENTIFICATION METHOD:
    ( D ) OTHER INFORMATION: /note="Gly or Gln, which may be modified at the amino terminal by C2-C18 alkylcarbonyl group"

( i x ) FEATURE:
    ( A ) NAME/KEY: modified-site
    ( B ) LOCATION: 4
    ( C ) IDENTIFICATION METHOD:
    ( D ) OTHER INFORMATION: /note="Leu, Nle or Phe, provided that this amino acid is not Leu when the amino acid at location 5 is Met, the amino acid at location 7 is Asn, the amino acid at location 8 is Leu, and the amino acids at locations 22 and 23 are both His"

( i x ) FEATURE:
    ( A ) NAME/KEY: modified-site
    ( B ) LOCATION: 5
    ( C ) IDENTIFICATION METHOD:
    ( D ) OTHER INFORMATION: /note="Met, Leu or Nle"

( i x ) FEATURE:
    ( A ) NAME/KEY: modified-site
    ( B ) LOCATION: 7
    ( C ) IDENTIFICATION METHOD:
    ( D ) OTHER INFORMATION: /note="Ala, Ser, Leu, Asn, Asp or Gln"

( i x ) FEATURE:
    ( A ) NAME/KEY: modified-site
    ( B ) LOCATION: 8
    ( C ) IDENTIFICATION METHOD:
    ( D ) OTHER INFORMATION: /note="Leu, Glu or Lys"

( i x ) FEATURE:
    ( A ) NAME/KEY: modified-site
    ( B ) LOCATION: 22
    ( C ) IDENTIFICATION METHOD:
    ( D ) OTHER INFORMATION: /note="His, Lys or Arg"

( i x ) FEATURE:
    ( A ) NAME/KEY: modified-site
    ( B ) LOCATION: 23

(C) IDENTIFICATION METHOD:
(D) OTHER INFORMATION: /note="His, Lys, or Arg"

(ix) FEATURE:
(A) NAME/KEY: modified-site
(B) LOCATION: 31
(C) IDENTIFICATION METHOD:
(D) OTHER INFORMATION: /note="Ala modified at the carboxy terminal with an amino group"

(xi) SEQUENCE DESCRIPTION: SEQ ID NO:6:

Ser Glu Xaa Xaa Xaa His Xaa Xaa Gly Lys Ser Ile Gln Asp Leu
1               5                   10                  15

Arg Arg Arg Phe Phe Leu Xaa Xaa Leu Ile Ala Glu Ile His Thr
                20                  25                  30

Xaa

PARATHYROID HORMONE ANTAGONISTS

The present invention relates to novel parathyroid hormone antagonists.

Parathyroid hormone (PTH) is an important hormone controlling the calcium metabolism in living bodies. Recently, analogous peptides having an activity similar to PTH, referred to as "parathyroid hormone related peptides" (PTHrP), have been discovered. Human PTHrP is a polypeptide consisting of 141 amino acids, and its PTH-like biological activities, namely elevation of blood level of calcium, acceleration of bone resorption, lowering of blood level of phosphorus, lowering of urine level of calcium, increase of urine level of cAMP, and renal activation of hydroxylase at the 1-position of vitamin D, have recently been reported [Horiuchi, et al., Science, Vol. 238, 1988; Kemp, et al., Science, Vol. 238, 1988].

It is known that PTH fragments which lack several amino acids at the amino terminal and carboxy terminal of PTH, such as PTH (3-34), PTH (7-34) or their derivatives inhibit the PTH action, and they are useful as PTH antagonists. Similar inhibitory action has also been reported on PTHrP fragments [Suva et al., Science, Vol. 237, 893 (1987); Rabbani et al., Report at the Meeting of American Bony Metabolism 1988].

European Patent Publication No. 341,962 discloses, as a human humoral hypercalcemic factor (hHGF), PTH derivatives such as hPTHrP(8-34)NH$_2$, hPTHrP(14-34)NH$_2$, and the like. However, they show insufficient activity for clinical use.

As the result of extensive study for the purpose of obtaining PTHrP derivatives showing more potent PTH antagonistic activity than known PTH or PTHrP derivatives, such as [Tyr$^{34}$]-hPTH (3-34)-NH$_2$, hPTHrP (3-34)-NH$_2$ and [Leu$^{11}$,D-Trp$^{12}$]-hPTHrP(7-34)-NH$_2$, the present inventors have found that a certain class of PTHrP derivatives possess excellent antagonistic activity against PTH.

Thus, the present invention provides the peptide derivatives of the following general formula (I) and identified in the attached Sequence Listing as SEQ ID Nos. 1-6.:

AAA BBB CCC DDD EEE FFF His GGG HHH Gly Lys Ser    (I)
1            5                    10

Ile Gln Asp Leu Arg Arg Arg Phe Phe Leu III JJJ Leu Ile Ala
15              20                 25

Glu Ile His Thr Xaa
30 wherein AAA is deletion or Ser, BBB is deletion or Glu, CCC is deletion, Ile, Phe, Leu, cyclohexylalanine, D-alle or Lys substituted at the ε-position by C$_6$-C$_{18}$ alkylcarbonyl group, DDD is Gly or Gln, EEE is Leu, Nle or Phe, FFF is Met, Leu or Nle, GGG is Ala, Ser, Leu, Asn, Asp or Gln, HHH is Leu, Glu or Lys, III is His, Lys or Arg, JJJ is His, Lys or Arg, Xaa is Ala modified at the carboxy terminal with an amino group, provided that CCC and DDD may independently be modified at the amino terminal by C$_2$-C$_{18}$ alkylcarbonyl group, and that EEE is not Leu when FFF is Met, GGG is Asn, HHH is Leu, III and JJJ are His, and the salts thereof.

The present invention will be explained in detail below.

The peptide derivatives of the invention are represented by the above-mentioned formula (I), i.e., SEQ ID No. 1. In the definition of the formula (I), specific examples of the C$_2$-C$_{18}$ alkylcarbonyl group are acetyl propionyl, butyryl, isobutyryl, valeryl, isovaleryl, pivaloyl, hexanoyl, 3-methylvaleryl (3-methylpentanoyl), heptanoyl, octanoyl, nonanoyl, decanoyl, lauroyl, myristoyl, palmitoyl and stearoyl, and the C$_5$-C$_{18}$ alkylcarbonyl group includes the above-noted groups which contains from 5 to 18 carbon atoms.

As previously stated, PTH or PTHrP fragments which lack 2-13 amino acid residues at the amino terminal show antagonistic property against PTH or PTHrP. However, such antagonistic activities are generally weak for practical use. Accordingly, development of peptide compounds having more potent antagonistic activity has long been desired. For this purpose, it is a general procedure to substitute one or more amino acids of PTH or PTHrP and then examine the activity of the resultant products. However, it is very difficult to previously estimate the result of particular substitutions. In addition, substitution of plural amino acids does not always bring about additive or synergistic effect expected from the known results in each substitution. Thus, it is far more difficult to previously estimate the results of a combination of two or more substitutions.

Under such circumstances as mentioned above, the inventors of the present invention synthesized and investigated a vast amount of PTHrP derivatives and found that the above-mentioned PTHrP derivatives of the formula (I) exhibited very potent antagonistic activity.

One of the key elements of the substitution of the amino acid or acids of PTHrP was introduction of a hydrophobic substituent at the 5- and 8- positions of naturally-occurring PTHrP and also substitution of other amino acid or acids so that the increased antagonistic activity due to the just-mentioned introduction of a hydrophobic substitution may be retained or enhanced. Another key element was introduction of a strong hydrophobic substituent into the N-terminal, which was accomplished by introduction of an amino acid bearing a hydrophobic acyl group into the N-terminal. Such substitution as mentioned above appears effective for both increase of activity and stabilization of the derivatives in a living body.

Illustrative examples of the PTHrP derivatives of the present invention are those as shown hereinafter in Table 2. These derivatives can also be converted to pharmacologically acceptable salts such as hydrochloride, acetate or the like, without loss of the activity.

The abbreviations used in the present specification have the following significances. All the amino acids have the L-form, unless otherwise stated.

Asp : Aspartic acid
Thr : Threonine
Ser : Serine
Glu : Glutamic acid
Asn : Asparagine
Gln : Glutamine
Gly : Glycine
Ala : Alanine
Met : Methionine
Met(O) : Methionine sulfoxide
Ile : Isoleucine
Leu : Leucine
Phe : Phenylalanine
Tyr : Tyrosine Lys : Lysine
His : Histidine
Arg : Arginine
Cha : β-Cyclohexylalanine
Nle : Norleucine
aIle : Alloisoleucine
Lys(Pal) : ε-palmitoyllysine
Lys(Myr) : ε-Myristoyllysine
Lys(Cap) : ε-Decanoyllysine
Lys(Hex) : ε-Hexanoyllysine
Ac : Acetyl
Mpa : 3-Methylpentanoyl
Hex : n-Hexanoyl
Cap : n-Decanoyl
Myr : Myristoyl
Pal : Palmitoyl
Boc : t-Butyloxycarbonyl
Z : Benzyloxycarbonyl
OcHx : Cyclohexyl ester
OBzl : Benzyl ester
Bzl : Benzyl
Bom : Benzyloxymethyl
Tos : p-Toluenesulfonyl
Cl-Z : 2-Chlorobenzyloxycarbonyl
Bop Reagent : Benzotriazo-1-yl-tris(dimethylamino)-phosphonium hexafluorophosphate The PTHrP derivatives (I) of the present invention can be prepared by repeating the condensation reaction of each protected amino acids in the order of amino acid sequence represented by the formula (I), starting from the C-terminal, in accordance with the solid phase peptide synthesis generally adopted, and then subjecting the resultant protected peptides to acid decomposition, aminolysis or known other procedures for removing the protecting groups and solid carrier used. The derivatives can also be prepared by condensing various peptide fragments according to so-called liquid phase synthetic methods. These general synthetic methods are described in detail in various literatures and text books [Izumiya, et al., "Fundamentals and Practice of Peptide Synthesis", Maruzen, 1985: Gross & Meienhofer, "The Peptides", Vol. 2, Academic Press, 1980].

Solid carriers usable for synthesizing the peptide of the present invention are those conventionally used for the peptide synthesis. Specific examples of the carriers include substituted benzyl type polystyrene resins, hydroxymethylphenylacetamide type polystyrene resins, substituted benzhydryl polystyrene resins and polyacrylamide resins capable of binding to a peptide. The condensation of amino acids can be attained in a conventional manner used for peptide synthesis, for example, dicyclohexylcarbodiimide (DCC) method, acid anhydride method, activated ester method, or a method using Bop reagent. Protecting groups used for protecting amino acids as starting materials are those already known in the peptide synthesis, which are easily removable by known means such as acid decomposition or the like. Examples of protecting groups for an amino group in the side chain are trifluoroacetyl, benzyloxycarbonyl and substituted benzyloxycarbonyl, such as (ortho- or para-)chlorobenzyloxycarbonyl, (ortho- or para-)bromobenzyloxycarbonyl or the like. Protecting groups for an α-amino group are those comparatively instable to an acid and include t-butoxycarbonyl, t-amyloxycarbonyl, p-methoxybenzyloxycarbonyl or the like. A carboxy group is protected by an ester group. Examples thereof are benzyl ester, substituted benzyl ester, alkyl ester such as cyclohexyl ester, cycloheptyl ester or the like. A guanidino group can be used without protection, or in the protected form with nitro or arylsulfonyl, such as tosyl, methoxybenzenesulfonyl, mesitylenesulfonyl or the like. Tosyl, benzyl, dinitrophenyl, benzyloxymethyl or the like may be used for protecting an imidazole. A hydroxy group of serine and threonine can be used without protection or after protection with benzyl, substituted benzyl or the like. An indole group of tryptophane is used without protection or after protection with formyl or the like.

The final deprotection and separation of the resultant peptide from the solid carrier can be conducted by the use of dry hydrogen fluoride in the presence of various scavengers. The scavengers mean those generally used for peptide synthesis and illustratively include anisole, (ortho-, meta- or para-)cresol, dimethyl sulfoxide, thiocresole, ethanedithiol, mercaptopyridine and the like.

Elongation and deprotection of the resultant peptide can be performed in accordance with FMOC method (Fields et al. Int. J. Pept. Protein Res. 35, 16, 1990). Purification of the peptide may be performed by gel filtration, ion exchange chromatography, reversed phase chromatography under high or low pressure.

Purified peptides can be converted into their salts by gel chromatography equilibrated with an aqueous acid solution.

The PTHrP derivatives (I) of the present invention may be useful as a therapeutic agent for treating dysbolism associated with calcium or phosphoric acid, such as hypercalcemia, osteoporosis, hyperparathyroidism, renal osteodystrophy, and the like, and other related diseases involving PTH or PTHrP.

The following detailed examples are presented by way of illustration of certain specific embodiments of the invention. The examples are representative only and should not be construed as limiting the present invention in any aspect.

EXAMPLE 1

Preparation of
Ile-Gln-Leu-Met-His-Asp-Lys-Gly-Lys-Ser-Ile-Gln-Asp-Leu-Arg-Arg-Arg-Phe-Phe-Leu-His-His-Leu-Ile-Ala-Glu-Ile-His-Thr-Ala-NH$_2$ ([Ile$^5$, Met$^8$]-hPTHrP (5-34)-NH$_2$; Compound No. 15 in Table 2): Seq. ID. No. 3

This peptide was synthesized on 1% cross-linked 4-methylbenzhydrylamine polystyrene solid phase carrier (amino group content 0.5 mmol) in accordance with the solid phase synthetic method as previously mentioned. The following amino acid derivatives were used for preparing this peptide.

Boc-Ala, Boc-Asp (OcHx), Boc-Asn, Boc-Arg (Tos), Boc-Gly, Boc-Glu (OcHx), Boc-Gln, Boc-His (Bom), Boc-Ile, Boc-Leu, Boc-Lys (Cl-Z), Boc-Met, Boc-Phe, Boc-Ser (Bzl), Boc-Thr (Bzl).

Elongation of the peptide chain was performed by repeating the procedure as shown in Table 1.

TABLE 1

| Treating method | Times treated | Period (min) |
|---|---|---|
| Deprotection | | |
| 1. Wash with CH$_2$Cl$_2$ | 1 | 1.0 |
| 2. Wash with 50% CF$_3$COOH/CH$_2$Cl$_2$ | 1 | 5.0 |
| 3. Deprotect with 50% CF$_3$COOH/CH$_2$Cl$_2$ | 1 | 25 |
| 4. Wash with CH$_2$Cl$_2$ | 1 | 1.0 |
| Neutralization | | |
| 1. 10% diisopropylethylamine/CH$_2$Cl$_2$ | 2 | 2.0 |

TABLE 1-continued

| Treating method | Times treated | Period (min) |
|---|---|---|
| 2. Wash with $CH_2Cl_2$ | 2 | 5.0 |
| 3. Wash with dimethylformamide | 5 | 1.0 |
| Condensation* | | |
| 1. sym-acid anhydride of tert-Butoxy-carbonylamino acid(2 mol equiv)**/ dimethylformamide | 1 | 30-60 |
| 2. Wash with dimethylformamide | 5 | 1.0 |
| 3. Wash with $CH_2Cl_2$ | 5 | 1.0 |

*Boc-Asn, Boc-Gln, Boc-Arg (Tos) and Boc-His (Bom) were subjected to DCC/HOBt method [Mojsov et al., J. Org. Chem., 45, 555 (1980)]. Boc-Asn, Boc-Gln, Boc-Arg (Tos), Boc-Ile, Boc-Thr (Bzl) and Boc-His (Bom) were subjected to condensation twice.
**sym-Acid anhydride obtained by mixing the protected amino acids with DCC was used without isolation.

Removal of the solid carrier and protecting group was performed by known HF method. More particularly, the protected peptide bound to polystyrene was reacted with a mixture of 10% p-cresole, 5% dimethylsulfide, and 85% dry hydrogen fluoride at 0° C. for one hour, and the reaction mixture was concentrated under reduced pressure. The residue was washed with ethyl acetate and extracted with 1M acetic acid. The extract was lyophilized to give crude peptide. The crude peptide was subjected to reversed phase high performance liquid chromatography and eluted with 0.1% trifluoroacetic acid-acetonitrile in linear gradient. After lyophilization of relevant fractions, the partially purified peptide was subjected to CM Toyopearl 650S (1.5×20 cm) in 20 mM ammonium acetate (pH 6.0) and eluted with 20 mM-1.0M ammonium acetate in linear gradient of ion concentration. The fractions containing the peptide was lyophilized, subjected to gel filtration with Sephadex G 25 (1.5×40 cm), which was equilibrated with 2% acetic acid, for conversion into the acetate and lyophilized to give the pure product.

Yield: 40.0 mg

Amino acid analysis: The peptide sample was hydrolyzed in 5.5 M hydrochloric acid at 110° C. for 48 hours and subjected to the amino acid analysis. The data within the parenthesis below represent calculated values. Correction for compensating possible decomposition of amino acids during the hydrolysis was not made.

Asp: 1.97 (2), Thr: 0.93 (1), Ser: 0.80 (1), Glu: 3.11 (3), Gly: 1.02 (1), Ala: 2.10 (2), Met: 0.94 (1), Ile: 3.74 (4), Leu: 3.98 (4), Phe: 2.06 (2), Lys: 1.91 (2), His: 3.79 (4), Arg: 3.27 (3)

Optical Rotation $[\alpha_D^{25}$: $-57.4°$ (C.=0.1, 1 M AcOH)

The following peptides listed in Table 2 were synthesized in the same method as in Example 1.

TABLE 2

| Compound | AAA | BBB | CCC | DDD | EEE | FFF | GGG | HHH | III | JJJ | Optical Rotation $[\alpha]_D^{25}$ (c 0.1) |
|---|---|---|---|---|---|---|---|---|---|---|---|
| 1 | Ser | Glu | Ile | Gln | Leu | Met | Ala | Leu | His | His | −61.3° |
| 2 | Ser | Glu | Ile | Gln | Leu | Met | Gln | Leu | His | His | −56.9° |
| 3 | Ser | Glu | Ile | Gln | Leu | Met | Leu | Leu | His | His | −56.7° |
| 4 | Ser | Glu | Ile | Gln | Leu | Met | Ser | Leu | His | His | −68.5° |
| 5 | Ser | Glu | Ile | Gln | Leu | Met | Asn | Glu | His | His | −54.0° |
| 6 | Ser | Glu | Ile | Gln | Leu | Leu | Asp | Lys | His | His | −63.8° |
| 7 | — | — | D—aIle | Gln | Leu | Met | Asp | Lys | His | His | −58.1° |
| 8 | — | — | Phe | Gln | Leu | Met | Asp | Lys | His | His | −52.2° |
| 9 | — | — | Leu | Gln | Leu | Met | Asp | Lys | His | His | −62.1° |
| 10 | — | — | — | Myr—Gln | Leu | Met | Asp | Lys | His | His | −46.7° |
| 11 | — | — | Cha | Gln | Leu | Met | Asp | Lys | His | His | −78.3° |
| 12 | — | — | Ile | Gly | Leu | Met | Asp | Lys | His | His | −44.0° |
| 13 | — | — | Ile | Gln | Phe | Met | Asp | Lys | His | His | −64.4° |
| 14 | — | — | Ile | Gln | Nle | Met | Asp | Lys | His | His | −66.0° |
| 15 | — | — | Ile | Gln | Leu | Met | Asp | Lys | His | His | −57.4° |
| 16 | — | — | Ile | Gln | Leu | Nle | Asp | Lys | His | His | −62.5° |
| 17 | — | — | Ile | Gln | Leu | Met | Ala | Lys | His | His | −69.9° |
| 18 | — | — | Ile | Gln | Leu | Met | Ala | Leu | His | His | −61.5° |
| 19 | — | — | Ile | Gln | Leu | Met | Asp | Lys | Arg | His | −52.0° |
| 20 | — | — | Ile | Gln | Leu | Met | Asp | Lys | His | Lys | −61.8° |
| 21 | — | — | Ac—Ile | Gln | Leu | Met | Asp | Lys | His | His | −74.9° |
| 22 | — | — | Myr—Ile | Gln | Leu | Met | Asp | Lys | His | His | −44.6° |
| 23 | — | — | Mpa—Ile | Gln | Leu | Met | Asp | Lys | His | His | −61.3° |
| 24 | — | — | Cap—Ile | Gln | Leu | Met | Asp | Lys | His | Lys | −54.5° |
| 25 | — | — | Ac—Lys(Myr) | Gln | Leu | Met | Asp | Lys | His | Lys | −47.0° |
| 26 | — | — | Ac—Lys(Hex) | Gln | Leu | Met | Asp | Lys | His | Lys | −61.9° |
| 27 | — | — | Ac—Lys(Cap) | Gln | Leu | Met | Asp | Lys | His | Lys | −49.5° |
| 28 | — | — | Ac—Lys(Pal) | Gln | Leu | Met | Asp | Lys | His | Lys | −39.0° | a: Measured in 1M acetic acid. "c" in the parenthesis denotes the weight of the peptide contained. The peptide content was determined by amino acid analysis.

EXPERIMENT 1

Determination of PTH antagonism

PTH antagonism of the PTHrP derivatives (I) of the present invention was determined on the basis of the output of cAMP, using cultured mouse osteoblast MC3T3-E1.

To a multiwell-culture plate of 12-well were inoculated $1 \times 10^5$ cells/well of the cultured cells, and the plate was incubated at 37° C. under 95% air-5% $CO_2$ atmosphere for 3 days after addition of α-modified MEM containing 10% semi-fetal bovine serum as a medium. Then, the medium was exchanged with α-modified MEM containing 1% bovine serum albumin and the cultured cells were incubated for 6 hours. The medium was replaced by α-modified MEM containing various concentrations of the compound of the present invention, $5 \times 10^{-9}$ M hPTH (1-34), 1% bovine serum albumin and 1 mM isobutylmethylxanthin, and the mixture was incubated for 1 hour. The medium was separated from the cells, and the medium was used as a sample for assaying cAMP. The cells were shaken with 90% n-propyl alcohol to extract cAMP according to Yamaguchi et al., J. Biol. Chem., 262, 7711-7718 (1987) for preparing another sample.

Assay of cAMP was performed using a commercially available cAMP-radioimmunoassay kit. Tables 3 and 4 below show 50% inhibition ($IC_{50}$) of the output of cAMP due to the compound of the present invention, when the amount of cAMP produced by $5 \times 10^{-9}$ M hPTH (1-34) is regarded as 100%. Compound numbers in the tables correspond to those in Table 2. [$Tyr^{34}$]-hPTH (3-34)-$NH_2$ and hPTHrP (3-34)-$NH_2$, both of which are heretofore known as a PTH antagonist, were used as active controls in Table 3, while Compound No. 15 was used as a control in Table 4.

TABLE 3

| Compound | $IC_{50}$ Ratio |
| --- | --- |
| (Tyr34)-hPTH(3-34)-$NH_2$ | 1 |
| hPTHrP(3-34)-$NH_2$ | 0.087 |
| Compound No. 1 | 0.003 |
| Compound No. 2 | 0.003 |
| Compound No. 8 | 0.026 |
| Compound No. 15 | 0.017 |

TABLE 4

| Compound | $IC_{50}$ Ratio |
| --- | --- |
| (Leu11,D-Trp12)-hPTHrP(7-34)-$NH_2$ | 3.91 |
| Compound No. 9 | 1.02 |
| Compound No. 10 | 2.24 |
| Compound No. 14 | 0.922 |
| Compound No. 15 | 1 |
| Compound No. 16 | 0.930 |
| Compound No. 17 | 1.17 |
| Compound No. 18 | 1.97 |
| Compound No. 19 | 0.934 |
| Compound No. 20 | 1.01 |
| Compound No. 21 | 0.934 |
| Compound No. 22 | 0.765 |
| Compound No. 25 | 0.343 |

As shown in Table 3 above, Compound No. 1 of the present invention showed 50% inhibition at a concentration of below about 1/300 of [$Tyr^{34}$]-hPTH (3-34)-$NH_2$ and at a concentration of about 1/29 of hPTHrP (3-34)-$NH_2$ when MC3T3-El was used.

Thus, the PTHrP derivatives (I) of the present invention are useful as a therapeutic agent for treating dysbolism associated with calcium or phosphoric acid, such as hypercalcemia, osteoporosis, hyperparathyroidism, renal osteodystrophy, and the like, and other related diseases involving PTH or PTHrP.

---

What is claimed is:
1. Peptide derivatives of the general formula (I):

AAA BBB CCC DDD EEE FFF His GGG HHH Gly Lys Ser    (I)
1               5                   10

Ile Gln Asp Leu Arg Arg Arg Phe Phe Leu III JJJ Leu Ile Ala
    15                  20                  25

Glu Ile His Thr Xaa
                30 wherein AAA is deletion, BBB is deletion, CCC is Ile which is substituted at the amino terminal by a $C_2$-$C_{18}$ alkylcarbonyl group or Lys which is substituted at the ε-position by a $C_6$-$C_{18}$ alkylcarbonyl group and substituted at the amino terminal by a $C_2$-$C_{18}$ alkylcarbonyl group, DDD is Gln, EEE is Leu, FFF is Met, GGG is Asp, HHH is Lys, III is His, JJJ is His or Lys and Xaa is Ala which is modified at the carboxy terminal with an amino group, or the salts thereof.

* * * * *